United States Patent
Zhou et al.

(10) Patent No.: US 6,967,178 B2
(45) Date of Patent: *Nov. 22, 2005

(54) ELASTIC STRAND LAMINATE

(75) Inventors: Peiguang Zhou, Appleton, WI (US); Cristian M. Neculescu, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 215 days.

This patent is subject to a terminal disclaimer.

(21) Appl. No.: 10/330,001

(22) Filed: Dec. 26, 2002

(65) Prior Publication Data

US 2004/0005835 A1 Jan. 8, 2004

Related U.S. Application Data

(63) Continuation-in-part of application No. 10/187,681, filed on Jul. 2, 2002.

(51) Int. Cl.[7] .......................... B32B 27/04; B32B 27/12
(52) U.S. Cl. ................ 442/149; 442/104; 442/328; 442/329; 442/382; 442/394; 442/400; 442/401; 428/343; 428/355 R
(58) Field of Search ............................. 442/104, 149, 442/328, 329, 382, 394, 400, 401; 428/343, 355 R

(56) References Cited

U.S. PATENT DOCUMENTS

| | | | |
|---|---|---|---|
| 2,206,761 A | 7/1940 | Bergstein | |
| 2,266,761 A | 12/1941 | Jackson, Jr. et al. | |
| 2,357,392 A | 9/1944 | Francis, Jr. | |
| 2,464,301 A | 3/1949 | Francis, Jr. | |
| 2,483,405 A | 10/1949 | Francis, Jr. | |
| 2,957,512 A | 10/1960 | Wade et al. | |
| 2,957,852 A | 10/1960 | Frankenburg et al. | |
| 3,186,893 A | 6/1965 | Mercer | |
| 3,338,992 A | 8/1967 | Kinney | |
| 3,341,394 A | 9/1967 | Kinney | |

(Continued)

FOREIGN PATENT DOCUMENTS

| | | | |
|---|---|---|---|
| CA | 2165486 | 6/1996 | ............... C09J/7/02 |
| DE | 34 23 644 | 1/1986 | ........... A41B/13/02 |
| DE | 37 34 963 | 4/1988 | ........... C08L/21/00 |
| EP | 0 155 636 | 9/1985 | ........... A41B/13/02 |
| EP | 0 172 037 | 2/1986 | ........... A41B/13/02 |
| EP | 0 217 032 | 4/1987 | .......... D04H/13/00 |
| EP | 0 239 080 | 9/1987 | ............. D01F/6/30 |
| EP | 0 330 716 A2 | 9/1989 | |

(Continued)

*Primary Examiner*—Terrel Morris
*Assistant Examiner*—Andrew T. Piziali
(74) *Attorney, Agent, or Firm*—Pauley Petersen & Erickson

(57) ABSTRACT

An elastic strand laminate, and a method of making an elastic strand laminate. The elastic strand laminate includes a plurality of self-adhering elastic strands made up of an elastomeric adhesive composition. The self-adhering elastic strands can be laminated to one or more facing sheets using conventional hot melt equipment.

22 Claims, 5 Drawing Sheets

U.S. PATENT DOCUMENTS

| | | |
|---|---|---|
| 3,371,668 A | 3/1968 | Johnson |
| 3,391,048 A | 7/1968 | Dyer et al. |
| 3,439,085 A | 4/1969 | Hartmann |
| 3,449,187 A | 6/1969 | Bobkowicz |
| 3,468,748 A | 9/1969 | Bassett |
| 3,489,148 A | 1/1970 | Duncan et al. |
| 3,502,538 A | 3/1970 | Petersen |
| 3,502,763 A | 3/1970 | Hartmann |
| 3,542,615 A | 11/1970 | Dobo et al. |
| 3,575,782 A | 4/1971 | Hansen |
| 3,616,129 A | 10/1971 | Sager |
| 3,629,047 A | 12/1971 | Davison |
| 3,669,823 A | 6/1972 | Wood |
| 3,673,026 A | 6/1972 | Brown |
| 3,676,242 A | 7/1972 | Prentice |
| 3,689,342 A | 9/1972 | Vogt et al. |
| 3,692,618 A | 9/1972 | Dorschner et al. |
| 3,752,613 A | 8/1973 | Vogt et al. |
| 3,773,590 A | 11/1973 | Morgan |
| 3,802,817 A | 4/1974 | Matsuki et al. |
| 3,806,289 A | 4/1974 | Schwarz |
| 3,836,416 A | 9/1974 | Ropiequet |
| 3,838,692 A | 10/1974 | Levesque |
| 3,849,241 A | 11/1974 | Butin et al. |
| 3,855,046 A | 12/1974 | Hansen et al. |
| 3,857,144 A | 12/1974 | Bustin |
| 3,860,003 A | 1/1975 | Buell |
| 3,890,184 A | 6/1975 | Morgan |
| 3,904,465 A | 9/1975 | Haase et al. |
| 3,912,567 A | 10/1975 | Schwartz |
| 3,917,448 A | 11/1975 | Wood |
| 3,932,328 A | 1/1976 | Korpman |
| 3,949,128 A | 4/1976 | Ostermeier |
| 3,949,130 A | 4/1976 | Sabee et al. |
| 3,973,063 A | 8/1976 | Clayton |
| 3,978,185 A | 8/1976 | Buntin et al. |
| 3,979,050 A | 9/1976 | Cilia |
| 4,013,816 A | 3/1977 | Sabee et al. |
| 4,028,292 A | 6/1977 | Korpman |
| 4,038,346 A | 7/1977 | Feeney |
| 4,041,203 A | 8/1977 | Brock et al. |
| 4,080,348 A | 3/1978 | Korpman |
| 4,090,385 A | 5/1978 | Packard |
| 4,100,324 A | 7/1978 | Anderson et al. |
| 4,107,364 A | 8/1978 | Sisson |
| 4,135,037 A | 1/1979 | Udipi et al. |
| 4,148,676 A | 4/1979 | Paquette et al. |
| 4,209,563 A | 6/1980 | Sisson |
| 4,211,807 A | 7/1980 | Yazawa et al. |
| 4,239,578 A | 12/1980 | Gore |
| 4,241,123 A | 12/1980 | Shih |
| 4,248,652 A | 2/1981 | Civardi et al. |
| 4,259,220 A | 3/1981 | Bunnelle et al. |
| 4,285,998 A | 8/1981 | Thibodeau |
| 4,300,562 A | 11/1981 | Pieniak |
| 4,302,495 A | 11/1981 | Marra |
| 4,303,571 A | 12/1981 | Jansen et al. |
| 4,304,234 A | 12/1981 | Hartmann |
| 4,310,594 A | 1/1982 | Yamazaki et al. |
| 4,319,572 A | 3/1982 | Widlund et al. |
| 4,323,534 A | 4/1982 | DesMarais |
| 4,333,782 A | 6/1982 | Pieniak |
| 4,340,558 A | 7/1982 | Hendrickson |
| 4,340,563 A | 7/1982 | Appel et al. |
| 4,374,888 A | 2/1983 | Bornslaeger |
| 4,375,446 A | 3/1983 | Fujii et al. |
| 4,402,688 A | 9/1983 | Julemont |
| 4,405,397 A | 9/1983 | Teed |
| 4,413,623 A | 11/1983 | Pieniak |
| 4,417,935 A | 11/1983 | Spencer |
| 4,418,123 A | 11/1983 | Bunnelle et al. |
| 4,438,167 A | 3/1984 | Schwarz |
| 4,440,819 A | 4/1984 | Rosser et al. |
| 4,490,427 A | 12/1984 | Grant et al. |
| 4,496,417 A | 1/1985 | Haake et al. |
| 4,500,316 A | 2/1985 | Damico |
| 4,507,163 A | 3/1985 | Menard |
| 4,522,863 A | 6/1985 | Keck et al. |
| 4,525,407 A | 6/1985 | Ness |
| 4,543,099 A | 9/1985 | Bunnelle et al. |
| 4,548,859 A | 10/1985 | Kline et al. |
| 4,552,795 A | 11/1985 | Hansen et al. |
| 4,555,811 A | 12/1985 | Shimalla |
| 4,572,752 A | 2/1986 | Jensen et al. |
| 4,586,199 A | 5/1986 | Birring |
| D284,036 S | 6/1986 | Birring |
| 4,606,964 A | 8/1986 | Wideman |
| 4,618,384 A | 10/1986 | Sabee |
| 4,626,305 A | 12/1986 | Suzuki et al. |
| 4,636,419 A | 1/1987 | Madsen et al. |
| 4,640,859 A | 2/1987 | Hansen et al. |
| 4,644,045 A | 2/1987 | Fowells |
| 4,652,487 A | 3/1987 | Morman |
| 4,656,081 A | 4/1987 | Ando et al. |
| 4,657,793 A | 4/1987 | Fisher |
| 4,657,802 A | 4/1987 | Morman |
| 4,661,389 A | 4/1987 | Mudge et al. |
| 4,663,220 A | 5/1987 | Wisneski et al. |
| 4,666,543 A | 5/1987 | Kawano |
| 4,675,068 A | 6/1987 | Lundmark |
| 4,683,877 A | 8/1987 | Ersfeld et al. |
| 4,687,477 A | 8/1987 | Suzuki et al. |
| 4,692,368 A | 9/1987 | Taylor et al. |
| 4,692,371 A | 9/1987 | Morman et al. |
| 4,698,242 A | 10/1987 | Salerno |
| 4,704,116 A | 11/1987 | Enloe |
| 4,718,901 A | 1/1988 | Singheimer |
| 4,719,261 A | 1/1988 | Bunnelle et al. |
| 4,720,415 A | 1/1988 | Vander Wielen et al. |
| 4,725,468 A | 2/1988 | McIntyre |
| 4,726,874 A | 2/1988 | VanVliet |
| 4,734,311 A | 3/1988 | Sokolowski |
| 4,734,320 A | 3/1988 | Ohira et al. |
| 4,734,447 A | 3/1988 | Hattori et al. |
| 4,735,673 A | 4/1988 | Piron |
| 4,756,942 A | 7/1988 | Aichele |
| 4,761,198 A | 8/1988 | Salerno |
| 4,762,582 A | 8/1988 | de Jonckheere |
| 4,775,579 A | 10/1988 | Hagy et al. |
| 4,777,080 A | 10/1988 | Harris, Jr. et al. |
| 4,781,966 A | 11/1988 | Taylor |
| 4,787,699 A | 11/1988 | Moulin |
| 4,789,699 A | 12/1988 | Kieffer et al. |
| 4,795,668 A | 1/1989 | Krueger et al. |
| 4,798,603 A | 1/1989 | Meyer et al. |
| 4,801,345 A | 1/1989 | Dussaud et al. |
| 4,801,482 A | 1/1989 | Goggans et al. |
| 4,803,117 A | 2/1989 | Daponte |
| 4,804,577 A | 2/1989 | Hazelton et al. |
| 4,818,464 A | 4/1989 | Lau |
| 4,818,597 A | 4/1989 | DaPonte et al. |
| 4,826,415 A | 5/1989 | Mende |
| 4,837,715 A | 6/1989 | Ungpiyakul et al. |
| 4,842,666 A | 6/1989 | Werenicz |
| 4,854,985 A | 8/1989 | Soderlund et al. |
| 4,854,989 A | 8/1989 | Singheimer |
| 4,863,779 A | 9/1989 | Daponte |
| 4,867,735 A | 9/1989 | Wogelius |
| 4,874,447 A | 10/1989 | Hazelton et al. |
| 4,879,170 A | 11/1989 | Radwanski et al. |
| 4,883,482 A | 11/1989 | Gandrez et al. |

| | | | | | | |
|---|---|---|---|---|---|---|
| 4,883,549 A | 11/1989 | Frost et al. | | 5,232,777 A | 8/1993 | Sipinen et al. |
| 4,891,258 A | 1/1990 | Fahrenkrug | | 5,236,430 A | 8/1993 | Bridges |
| 4,892,536 A | 1/1990 | DesMarais et al. | | 5,236,770 A | 8/1993 | Assent et al. |
| 4,892,903 A | 1/1990 | Himes | | 5,238,733 A | 8/1993 | Joseph et al. |
| 4,900,619 A | 2/1990 | Ostrowski et al. | | 5,246,433 A | 9/1993 | Hasse et al. |
| 4,906,507 A | 3/1990 | Grynaeus et al. | | D340,283 S | 10/1993 | Igaue et al. |
| 4,908,247 A | 3/1990 | Baird et al. | | 5,252,170 A | 10/1993 | Schaupp |
| 4,908,253 A | 3/1990 | Rasmussen | | 5,259,902 A | 11/1993 | Muckenfuhs |
| 4,910,064 A | 3/1990 | Sabee | | 5,260,126 A | 11/1993 | Collier, IV et al. |
| 4,917,696 A | 4/1990 | De Jonckheere | | 5,272,236 A | 12/1993 | Lai et al. |
| 4,917,746 A | 4/1990 | Kons et al. | | 5,277,976 A | 1/1994 | Hogle et al. |
| 4,929,492 A | 5/1990 | Carey, Jr. et al. | | 5,278,272 A | 1/1994 | Lai et al. |
| 4,935,021 A | 6/1990 | Huffman et al. | | 5,288,791 A | 2/1994 | Collier, IV et al. |
| 4,938,757 A | 7/1990 | Van Gompel et al. | | 5,290,842 A | 3/1994 | Sasaki et al. |
| 4,938,821 A | 7/1990 | Soderlund et al. | | 5,296,080 A | 3/1994 | Merkatoris et al. |
| 4,939,016 A | 7/1990 | Radwanski et al. | | 5,304,599 A | 4/1994 | Himes |
| 4,940,464 A | 7/1990 | Vam Gompel et al. | | 5,308,345 A | 5/1994 | Herrin |
| 4,949,668 A | 8/1990 | Heindel et al. | | 5,312,500 A | 5/1994 | Kurihara et al. |
| 4,965,122 A | 10/1990 | Morman | | 5,324,580 A | 6/1994 | Allan et al. |
| 4,968,313 A | 11/1990 | Sabee | | 5,332,613 A | 7/1994 | Taylor et al. |
| 4,970,259 A | 11/1990 | Mitchell et al. | | 5,334,437 A | 8/1994 | Zafiroglu |
| 4,977,011 A | 12/1990 | Smith | | 5,334,446 A | 8/1994 | Quantrille et al. |
| 4,981,747 A | 1/1991 | Morman | | 5,336,545 A | 8/1994 | Morman |
| 4,984,584 A | 1/1991 | Hansen et al. | | 5,336,552 A | 8/1994 | Strack et al. |
| 4,994,508 A | 2/1991 | Shiraki et al. | | 5,342,341 A | 8/1994 | Igaue et al. |
| 4,995,928 A | 2/1991 | Sabee | | 5,342,469 A | 8/1994 | Bodford et al. |
| 4,998,929 A | 3/1991 | Bjorksund et al. | | 5,360,854 A | 11/1994 | Bozich, Jr. |
| 5,000,806 A | 3/1991 | Merkatoris et al. | | 5,364,382 A | 11/1994 | Latimer et al. |
| 5,002,815 A | 3/1991 | Yamanaka et al. | | 5,366,793 A | 11/1994 | Fitts, Jr. et al. |
| 5,005,215 A | 4/1991 | McIlquham | | 5,376,198 A | 12/1994 | Fahrenkrug et al. |
| 5,013,785 A | 5/1991 | Mizui | | 5,376,430 A | 12/1994 | Swenson et al. |
| 5,028,646 A | 7/1991 | Miller et al. | | 5,382,400 A | 1/1995 | Pike et al. |
| 5,032,120 A | 7/1991 | Freeland et al. | | 5,385,775 A | 1/1995 | Wright |
| 5,034,008 A | 7/1991 | Breitkopf | | 5,389,173 A | 2/1995 | Merkatoris et al. |
| 5,045,133 A | 9/1991 | DaPonte et al. | | 5,389,438 A * | 2/1995 | Miller et al. .......... 428/355 RA |
| 5,046,272 A | 9/1991 | Vogt et al. | | 5,393,599 A | 2/1995 | Quantrille et al. |
| 5,057,368 A | 10/1991 | Largman et al. | | 5,399,219 A | 3/1995 | Roessler et al. |
| 5,060,349 A | 10/1991 | Walton et al. | | 5,405,682 A | 4/1995 | Shawyer et al. |
| 5,069,970 A | 12/1991 | Largman et al. | | 5,407,507 A | 4/1995 | Ball |
| 5,073,436 A | 12/1991 | Antonacci et al. | | 5,411,618 A | 5/1995 | Jocewicz, Jr. |
| 5,093,422 A | 3/1992 | Himes | | 5,413,654 A | 5/1995 | Igaue et al. |
| 5,096,532 A | 3/1992 | Neuwirth et al. | | 5,413,849 A | 5/1995 | Austin et al. |
| 5,100,435 A | 3/1992 | Onwumere | | 5,415,644 A | 5/1995 | Enloe |
| 5,104,116 A | 4/1992 | Pohjola | | 5,415,649 A | 5/1995 | Watanabe et al. |
| 5,108,820 A | 4/1992 | Kaneko et al. | | 5,415,925 A | 5/1995 | Austin et al. |
| 5,110,403 A | 5/1992 | Ehlert | | 5,422,172 A | 6/1995 | Wu |
| 5,112,889 A | 5/1992 | Miller et al. | | 5,425,987 A | 6/1995 | Shawver et al. |
| 5,114,087 A | 5/1992 | Fisher et al. | | 5,429,629 A | 7/1995 | Latimer et al. |
| 5,116,662 A | 5/1992 | Morman | | 5,429,694 A | 7/1995 | Herrmann |
| 5,145,727 A | 9/1992 | Potts et al. | | 5,429,856 A | 7/1995 | Krueger et al. |
| 5,147,487 A | 9/1992 | Nomura et al. | | 5,431,644 A | 7/1995 | Sipinen et al. |
| 5,149,741 A * | 9/1992 | Alper et al. ................. 525/95 | | 5,431,991 A | 7/1995 | Quantrille et al. |
| 5,163,932 A | 11/1992 | Nomura et al. | | 5,447,462 A | 9/1995 | Smith et al. |
| D331,627 S | 12/1992 | Igaue et al. | | 5,447,508 A | 9/1995 | Numano et al. |
| 5,169,706 A | 12/1992 | Collier, IV et al. | | 5,449,353 A | 9/1995 | Watanabe et al. |
| 5,169,712 A | 12/1992 | Tapp | | 5,464,401 A | 11/1995 | Hasse et al. |
| 5,176,668 A | 1/1993 | Bernardin | | 5,466,410 A | 11/1995 | Hills |
| 5,176,672 A | 1/1993 | Bruemmer et al. | | 5,472,775 A | 12/1995 | Obijeski et al. |
| 5,178,931 A | 1/1993 | Perkins et al. | | 5,476,458 A | 12/1995 | Glaug et al. |
| 5,186,779 A | 2/1993 | Tubbs | | 5,476,563 A | 12/1995 | Nakata |
| 5,188,885 A | 2/1993 | Timmons et al. | | 5,484,645 A | 1/1996 | Lickfield et al. |
| 5,192,606 A | 3/1993 | Proxmire et al. | | 5,486,166 A | 1/1996 | Bishop et al. |
| 5,198,281 A | 3/1993 | Muzzy et al. | | 5,490,846 A | 2/1996 | Ellis et al. |
| 5,200,246 A | 4/1993 | Sabee | | 5,496,298 A | 3/1996 | Kuepper et al. |
| 5,204,429 A | 4/1993 | Kaminsky et al. | | 5,498,468 A | 3/1996 | Blaney |
| D335,707 S | 5/1993 | Igaue et al. | | 5,500,075 A | 3/1996 | Herrmann |
| 5,209,801 A | 5/1993 | Smith | | 5,501,679 A | 3/1996 | Krueger et al. |
| 5,219,633 A | 6/1993 | Sabee | | 5,509,915 A | 4/1996 | Hanson et al. |
| 5,224,405 A | 7/1993 | Pohjola | | 5,514,470 A | 5/1996 | Haffner et al. |
| 5,226,992 A | 7/1993 | Morman | | 5,516,476 A | 5/1996 | Haggard et al. |
| 5,229,191 A | 7/1993 | Austin | | 5,523,146 A | 6/1996 | Bodford et al. |

| Patent | Date | Inventor | | Patent | Date | Inventor |
|---|---|---|---|---|---|---|
| 5,527,300 A | 6/1996 | Sauer | | 5,840,633 A | 11/1998 | Kurihara et al. |
| 5,531,850 A | 7/1996 | Herrmann | | 5,846,232 A | 12/1998 | Serbiak et al. |
| 5,534,330 A | 7/1996 | Groshens | | 5,849,001 A | 12/1998 | Torimae et al. |
| 5,536,563 A | 7/1996 | Shah et al. | | 5,856,387 A | 1/1999 | Sasaki et al. |
| 5,540,796 A | 7/1996 | Fries | | 5,858,515 A | 1/1999 | Stokes et al. |
| 5,540,976 A | 7/1996 | Shawver et al. | | 5,860,945 A | 1/1999 | Cramer et al. |
| 5,543,206 A | 8/1996 | Austin et al. | | 5,865,933 A | 2/1999 | Morin et al. |
| 5,545,158 A | 8/1996 | Jessup | | 5,876,392 A | 3/1999 | Hisada |
| 5,545,285 A | 8/1996 | Johnson | | 5,879,776 A | 3/1999 | Nakata |
| 5,549,964 A | 8/1996 | Shohji et al. | | 5,882,573 A | 3/1999 | Kwok et al. |
| 5,569,232 A | 10/1996 | Roe et al. | | 5,885,656 A | 3/1999 | Goldwasser |
| 5,575,783 A | 11/1996 | Clear et al. | | 5,885,686 A | 3/1999 | Cederblad et al. |
| 5,576,090 A | 11/1996 | Suzuki | | 5,897,546 A | 4/1999 | Kido et al. |
| 5,582,668 A | 12/1996 | Kling | | 5,899,895 A | 5/1999 | Robles et al. |
| 5,591,152 A | 1/1997 | Buell et al. | | 5,902,540 A | 5/1999 | Kwok |
| 5,591,792 A | 1/1997 | Hattori et al. | | 5,904,298 A | 5/1999 | Kwok et al. |
| 5,595,618 A | 1/1997 | Fries et al. | | 5,916,206 A | 6/1999 | Otsubo et al. |
| 5,597,430 A | 1/1997 | Rasche | | 5,921,973 A | 7/1999 | Newkirk et al. |
| 5,612,118 A | 3/1997 | Schleinz et al. | | 5,930,139 A | 7/1999 | Chapdelaine et al. |
| 5,614,276 A | 3/1997 | Petsetakis | | 5,931,581 A | 8/1999 | Garberg et al. |
| 5,620,780 A | 4/1997 | Krueger et al. | | 5,932,039 A | 8/1999 | Popp et al. |
| 5,624,740 A | 4/1997 | Nakata | | 5,938,648 A | 8/1999 | LaVon et al. |
| 5,626,573 A | 5/1997 | Igaue et al. | | 5,941,865 A | 8/1999 | Otsubo et al. |
| 5,628,856 A | 5/1997 | Dobrin et al. | | D414,262 S | 9/1999 | Ashton et al. |
| 5,645,672 A | 7/1997 | Dobrin | | 5,952,252 A | 9/1999 | Shawver et al. |
| 5,652,041 A | 7/1997 | Buerger et al. | | 5,964,970 A | 10/1999 | Woolwine et al. |
| 5,660,664 A | 8/1997 | Herrmann | | 5,964,973 A | 10/1999 | Heath et al. |
| 5,663,228 A | 9/1997 | Sasaki et al. | | 5,990,377 A | 11/1999 | Chen et al. |
| 5,669,897 A | 9/1997 | Lavon et al. | | 5,993,433 A | 11/1999 | St. Louis et al. |
| 5,674,216 A | 10/1997 | Buell et al. | | 5,997,521 A | 12/1999 | Robles et al. |
| 5,680,653 A | 10/1997 | Mathis et al. | | 6,004,306 A | 12/1999 | Robles et al. |
| 5,681,302 A | 10/1997 | Melbye et al. | | 6,009,558 A | 1/2000 | Rosch et al. |
| 5,683,787 A | 11/1997 | Boich et al. | | 6,033,502 A | 3/2000 | Coenen et al. |
| 5,690,626 A | 11/1997 | Suzuki et al. | | 6,045,543 A | 4/2000 | Pozniak et al. |
| 5,691,034 A | 11/1997 | Krueger et al. | | 6,048,326 A | 4/2000 | Davis et al. |
| 5,693,038 A | 12/1997 | Suzuki et al. | | 6,057,024 A | 5/2000 | Mleziva et al. |
| 5,695,849 A | 12/1997 | Shawver et al. | | 6,066,369 A | 5/2000 | Schulz et al. |
| 5,702,378 A | 12/1997 | Widlund et al. | | 6,087,550 A | 7/2000 | Anderson-Fischer et al. |
| 5,707,709 A | 1/1998 | Blake | | 6,090,234 A | 7/2000 | Barone et al. |
| 5,709,921 A | 1/1998 | Shawver | | 6,092,002 A | 7/2000 | Kastman et al. |
| 5,720,838 A | 2/1998 | Nakata | | 6,093,663 A | 7/2000 | Ouellette et al. |
| 5,733,635 A | 3/1998 | Terakawa et al. | | 6,096,668 A | 8/2000 | Abuto et al. |
| 5,733,822 A | 3/1998 | Gessner et al. | | 6,123,694 A | 9/2000 | Pieniak et al. |
| 5,735,839 A | 4/1998 | Kawaguchi et al. | | 6,132,410 A | 10/2000 | Van Gompel et al. |
| 5,736,219 A | 4/1998 | Suehr et al. | | 6,149,637 A | 11/2000 | Allen et al. |
| 5,746,731 A | 5/1998 | Hisada | | 6,152,904 A | 11/2000 | Matthews et al. |
| 5,749,865 A | 5/1998 | Yamamoto et al. | | 6,169,848 B1 | 1/2001 | Henry |
| 5,749,866 A | 5/1998 | Roe et al. | | 6,180,229 B1 * | 1/2001 | Becker et al. ........ 428/355 BL |
| 5,766,389 A | 6/1998 | Brandon et al. | | 6,183,587 B1 | 2/2001 | McFall et al. |
| 5,766,737 A | 6/1998 | Willey et al. | | 6,183,847 B1 | 2/2001 | Goldwasser |
| 5,769,838 A | 6/1998 | Buell et al. | | 6,197,845 B1 * | 3/2001 | Janssen et al. .............. 523/111 |
| 5,769,993 A | 6/1998 | Baldauf | | 6,214,476 B1 | 4/2001 | Ikeda et al. |
| 5,772,649 A | 6/1998 | Siudzinski | | 6,217,690 B1 | 4/2001 | Rajala et al. |
| 5,773,373 A | 6/1998 | Wynne et al. | | 6,231,557 B1 | 5/2001 | Krautkramer et al. |
| 5,773,374 A | 6/1998 | Wood et al. | | 6,238,379 B1 | 5/2001 | Keuhn, Jr. et al. |
| 5,788,804 A | 8/1998 | Horsting | | 6,245,050 B1 | 6/2001 | Odorzynski et al. |
| 5,789,065 A | 8/1998 | Haffner et al. | | 6,245,168 B1 | 6/2001 | Coenen et al. |
| 5,789,328 A | 8/1998 | Kurihara et al. | | 6,260,211 B1 | 7/2001 | Rajala et al. |
| 5,789,474 A | 8/1998 | Lu et al. | | 6,279,807 B1 | 8/2001 | Crowley et al. |
| 5,790,983 A * | 8/1998 | Rosch et al. ...................... 2/69 | | 6,290,979 B1 | 9/2001 | Roe et al. |
| 5,800,903 A | 9/1998 | Wood et al. | | 6,310,164 B1 | 10/2001 | Morizono et al. |
| 5,804,021 A | 9/1998 | Abuto et al. | | 6,316,013 B1 | 11/2001 | Paul et al. |
| 5,804,286 A | 9/1998 | Quantrille et al. | | 6,316,687 B1 | 11/2001 | Davis et al. |
| 5,814,176 A | 9/1998 | Proulx | | 6,316,688 B1 | 11/2001 | Hammons et al. |
| 5,817,087 A | 10/1998 | Takabayashi et al. | | 6,320,096 B1 | 11/2001 | Inoue et al. |
| 5,818,719 A | 10/1998 | Brandon et al. | | 6,323,389 B1 | 11/2001 | Thomas et al. |
| 5,830,203 A | 11/1998 | Suzuki et al. | | 6,329,459 B1 | 12/2001 | Kang et al. |
| 5,834,089 A | 11/1998 | Jones et al. | | 6,364,863 B1 | 4/2002 | Yamamoto et al. |
| 5,836,931 A | 11/1998 | Toyoda et al. | | 6,365,659 B1 | 4/2002 | Aoyama et al. |
| 5,836,932 A | 11/1998 | Buell et al. | | 6,367,089 B2 | 4/2002 | Van Gompel et al. |
| 5,840,412 A | 11/1998 | Wood et al. | | 6,475,600 B1 | 11/2002 | Morman et al. |

| | | | |
|---|---|---|---|
| 6,537,935 B1 | 3/2003 | Seth et al. | |
| 6,645,190 B1 | 11/2003 | Olson et al. | |
| 6,657,009 B2 | 12/2003 | Zhou | |
| 6,767,852 B2 | 7/2004 | Friderich et al. | |
| 2002/0002021 A1 | 1/2002 | May et al. | |
| 2002/0009940 A1 | 1/2002 | May et al. | |
| 2002/0019616 A1 | 2/2002 | Thomas | |
| 2002/0072561 A1 | 6/2002 | Johoji et al. | |
| 2002/0081423 A1 | 6/2002 | Heffelfinger | |
| 2002/0104608 A1 | 8/2002 | Welch et al. | |
| 2002/0122953 A1 | 9/2002 | Zhou | |
| 2002/0123538 A1 | 9/2002 | Zhou et al. | |
| 2002/0123726 A1 | 9/2002 | Zhou et al. | |
| 2002/0138063 A1 | 9/2002 | Kuen et al. | |
| 2002/0164465 A1 | 11/2002 | Curro et al. | |
| 2003/0232928 A1 | 12/2003 | Atwood et al. | |
| 2004/0127128 A1 | 7/2004 | Thomas | |

FOREIGN PATENT DOCUMENTS

| | | | |
|---|---|---|---|
| EP | 0 380 781 | 8/1990 | B05C/5/02 |
| EP | 0 396 800 | 11/1990 | A61F/13/56 |
| EP | 0 456 885 | 11/1991 | A61F/13/15 |
| EP | 0 547 497 | 6/1993 | A61F/13/15 |
| EP | 0 582 569 | 2/1994 | B32B/5/26 |
| EP | 0 604 731 | 7/1994 | B32B/31/00 |
| EP | 0 617 939 | 10/1994 | A61F/13/15 |
| EP | 0 688 550 | 12/1995 | A61F/13/15 |
| EP | 0 689 815 | 1/1996 | A61F/13/15 |
| EP | 0 713 546 | 5/1996 | D04H/13/00 |
| EP | 0 743 052 | 11/1996 | A61F/13/15 |
| EP | 0 753 292 | 1/1997 | A61F/13/15 |
| EP | 0 761 193 | 3/1997 | A61F/13/15 |
| EP | 0 761 194 | 3/1997 | A61F/13/15 |
| EP | 0 763 353 | 3/1997 | A61F/13/15 |
| EP | 0 787 474 | 8/1997 | A61F/13/15 |
| EP | 0 802 251 A1 | 10/1997 | |
| EP | 0 806 196 | 11/1997 | A61F/13/15 |
| EP | 0 814 189 | 12/1997 | D04H/13/00 |
| EP | 0 873 738 | 10/1998 | A61F/13/15 |
| EP | 0 888 101 | 1/1999 | A61F/13/15 |
| EP | 0 901 780 | 3/1999 | A61F/13/15 |
| EP | 1 013 251 | 6/2000 | A61F/13/15 |
| GB | 2 244 422 | 12/1991 | A61F/13/15 |
| GB | 2 250 921 | 6/1992 | A61F/13/15 |
| GB | 2 253 131 | 9/1992 | A61F/13/72 |
| GB | 2 267 024 | 11/1993 | A61F/13/66 |
| GB | 2 268 389 | 1/1994 | A61F/13/15 |
| IS | 92891 | 2/1992 | |
| JP | 3-67646 | 3/1991 | B32B/5/28 |
| WO | WO 80/00676 | 4/1980 | |
| WO | WO 90/03464 | 4/1990 | D04H/1/56 |
| WO | WO 91/07277 | 5/1991 | B32B/5/04 |
| WO | WO 92/16371 | 10/1992 | B32B/31/00 |
| WO | WO 93/15247 | 8/1993 | D04H/1/48 |
| WO | WO 93/17648 | 9/1993 | A61F/13/15 |
| WO | WO 94/09736 | 5/1994 | A61F/13/15 |
| WO | WO 95/03443 | 2/1995 | D04H/13/00 |
| WO | WO 95/04182 | 2/1995 | D04H/13/00 |
| WO | WO 95/16425 | 6/1995 | A61F/13/58 |
| WO | WO 95/16562 | 6/1995 | B32B/5/24 |
| WO | WO 95/34264 | 12/1995 | A61F/13/15 |
| WO | WO 96/13989 | 5/1996 | A41B/9/00 |
| WO | WO 96/23466 | 8/1996 | A61F/13/15 |
| WO | WO 96/35402 | 11/1996 | A61F/13/15 |
| WO | WO 97/17046 | 5/1997 | A61F/13/15 |
| WO | WO 98/14156 | 4/1998 | A61F/13/15 |
| WO | WO 98/49988 | 11/1998 | A61F/13/15 |
| WO | WO 98/55062 | 12/1998 | A61F/13/15 |
| WO | WO 99/17926 | 4/1999 | B32B/5/04 |
| WO | WO 99/24519 | 5/1999 | C09J/7/02 |
| WO | WO 99/47590 | 9/1999 | C08J/5/18 |
| WO | WO 99/60969 | 12/1999 | A61F/13/15 |
| WO | WO 99/60970 | 12/1999 | A61F/13/15 |
| WO | WO 99/60971 | 12/1999 | A61F/13/15 |
| WO | WO 00/10500 | 3/2000 | A61F/13/15 |
| WO | WO 00/29199 | 5/2000 | B29C/55/18 |
| WO | WO 00/37003 | 6/2000 | A61F/13/15 |
| WO | WO 00/37005 | 6/2000 | A61F/13/15 |
| WO | WO 00/37009 | 6/2000 | |
| WO | WO 00/37723 | 6/2000 | |
| WO | WO 00/59429 | 10/2000 | A61F/13/15 |
| WO | WO 01/00053 | 1/2001 | A41F/9/02 |
| WO | WO 01/32116 | 5/2001 | A61F/13/15 |
| WO | WO 01/49907 | 7/2001 | D01F/8/00 |
| WO | WO 01/87214 | 11/2001 | A61F/13/496 |
| WO | WO 02/34184 | 5/2002 | A61F/13/49 |
| WO | WO 02/053667 A2 | 7/2002 | |
| WO | WO 02/053668 A2 | 7/2002 | |
| WO | WO 02/060690 | 8/2002 | B32B/27/32 |
| WO | WO 02/085624 A1 | 10/2002 | |
| WO | WO 2004/039907 A1 | 5/2004 | |

* cited by examiner

ELASTIC STRAND LAMINATE

CROSS-REFERENCE TO RELATED APPLICATION

This application is a continuation-in-part application of U.S. patent application Ser. No. 10/187,681 filed Jul. 2, 2002.

BACKGROUND OF THE INVENTION

This invention is directed to an elastic strand laminate made up of elastic strands self-adhered to one or more facing sheets.

Personal care garments often include elasticized portions to create a gasket-like fit around certain openings, such as waist openings and leg openings. Elastic laminates can be used in the manufacture of such garments to avoid complicated elastic-attachment steps during the garment manufacturing process.

One type of elastomeric laminate is a stretch-bonded laminate that includes elastic strands produced from an extruder and bonded to a facing sheet or sheets using a hot melt adhesive. Laminates including pre-made elastic strands can be processed online but require an elastic attachment adhesive with high add-on in order to reduce strand slippage. The cost of making stretch-bonded laminates can be relatively high due to the cost of the facing sheet or sheets, plus the cost of the elastic strands, plus the cost of the adhesive.

Another type of elastomeric laminate can be made using a vertical filament laminate-stretch-bonded laminate (VFL-SBL) process. However, the VFL-SBL process must be in off-line operation due to process complexity.

Elastomeric adhesive compositions are multifunctional in the sense that they function as an elastomer in a nonwoven composite while also serving as a hot melt adhesive for bonding substrates. Elastomeric adhesive compositions in the form of elastomeric adhesive films are currently recognized as suitable for use in the manufacture of personal care articles. More particularly, elastomeric adhesive compositions can be used to bond facing materials, such as spunbond, to one another while simultaneously elasticizing the resulting laminate. The resulting laminate can be used to form an elastomeric portion of an absorbent article, such as a region surrounding a waist opening and/or a leg opening.

Non-woven elastic adhesive film laminates may require high output of adhesive add-on to achieve a tension target for product application. High add-on of the film laminate may generate a bulky, thick feel and appearance, and high cost. Furthermore, the high adhesive output requirement for the film formation would make on-line processing even more difficult due to the limitation of hot melt equipment output capacity. Also, such film lamination processes are relatively complex and need more precise control than strand lamination since a film edge thinning effect may cause the film to break during stretching.

Some elastomeric adhesive compositions lose their adhesiveness when the compositions are stretched and then bonded between two nonwoven substrates. The elasticity of these elastomeric adhesive compositions (in terms of tension decay) is negatively affected when laminates including the compositions are aged at elevated temperatures, for example around 130 degrees Fahrenheit, which is commonly experienced under hot boxcar storage conditions. It appears that the poor tension and adhesion of such elastomeric adhesive compositions results from the chosen base polymer, tackifier, and plasticizer chemistries as well as the unbalanced ratio of polymer to low molecular weight species in the formulation.

There is a need or desire for an elastic laminate having improved elastic and adhesion properties which can be made in a relatively simple process with reduced raw material usage while still providing adequate tension for product application.

SUMMARY OF THE INVENTION

In response to the discussed difficulties and problems encountered in the prior art, a new elastic strand laminate and a method of making such an elastic strand laminate have been discovered.

The present invention is directed to an elastic strand laminate having superior elastic and adhesion properties. The laminate includes strands of an elastomeric adhesive composition that is hot melt-processable and can be formed on-line. The strands can be self-adhered to one or more facing sheets without requiring additional adhesive. This laminate is particularly suitable for use in personal care product applications, medical garment applications, and industrial workwear garment applications.

The elastomeric adhesive composition from which the strands are made includes a base polymer and a high softening point tackifier resin. The composition may also include a low softening point additive, with the low softening point additive present in an amount of between about 0% and about 20% by weight. The composition may further include an antioxidant, with the antioxidant present in an amount of between about 0.1% and about 1.0% by weight. The tackifier suitably has a softening point of at least 80 degrees Celsius and a viscosity of at least 1500 cps at 360 degrees Fahrenheit, and may include hydrocarbons from petroleum distillates, rosin, rosin esters, polyterpenes derived from wood, and/or polyterpenes derived from synthetic chemicals. The base polymer may include polystyrene-polyethylene-polypropylene-polystyrene (SEPS) block copolymer, styrene-isoprene-styrene (SIS), styrene-butadiene-styrene (SBS) block copolymer, thermoplastic polyurethane, and/or ethylene-propylene-diene (EPDM) copolymer. The base polymer is suitably present in an amount between about 30% and about 75% by weight, and the high softening point tackifier is suitably present in an amount between about 30% and about 70% by weight. The elastomeric adhesive compositions suitably have a viscosity of about 5,000 to 80,000 cps at between 350 and 400 degrees Fahrenheit. The compositions may also include elastomeric polymer strands incorporated therein to provide added reinforcement and elasticity.

The strands of the elastomeric adhesive composition can be self-adhered to one or more facing sheets, suitably between two facing sheets of spunbond, meltblown, film, or other facing material. The strands can be spaced apart on the facing sheet(s) by about 5 to about 15 strands per inch, with each of the strands having a diameter or width of between about 0.1 and about 0.25 inch. The elastic strand laminates of the invention suitably have a basis weight between about 20 and about 120 grams per square meter. The elastic strand laminates of the invention significantly improve the rate and extent of tension decay, as well as adhesion properties of the spunbond laminates compared to spunbond laminates including conventional elastomeric adhesive compositions. Furthermore, the elastic strand laminates of the invention require a lower output of adhesive add-on, compared to elastic film laminates, to achieve a tension target for product application which also results in less bulk and lower cost.

The invention also includes a method of making these elastic strand laminates. The method includes the steps of forming a solid phase composition of the base polymer and the high softening point tackifier resin, then heating the solid phase composition to form a liquid phase composition. Conventional hot melt equipment can be used to heat the elastomeric adhesive composition. The strands are then formed by extruding the liquid phase composition through a strand die onto a chill roll set at a temperature of between about 10 and about 50 degrees Celsius. The resulting strands can be peeled off the chill roll while stretching the strands. The strands can be stretched between about 200% and about 1200%, at an output of between about 20 and about 150 grams per square meter before stretching, from the strand die. The strands can be self-adhered to one or more facing materials, such as a nonwoven web or film. Tension in the elastic strand laminate can be adjusted by adjusting an add-on level of the elastomeric adhesive composition, or adjusting a stretch ratio of the strands, or varying the diameters of the strands.

With the foregoing in mind, it is a feature and advantage of the invention to provide an elastic strand laminate having improved adhesion and elastic properties, which can be produced at a relatively low cost. The invention also includes methods of making such elastic strand laminates.

DEFINITIONS

Figure 1:
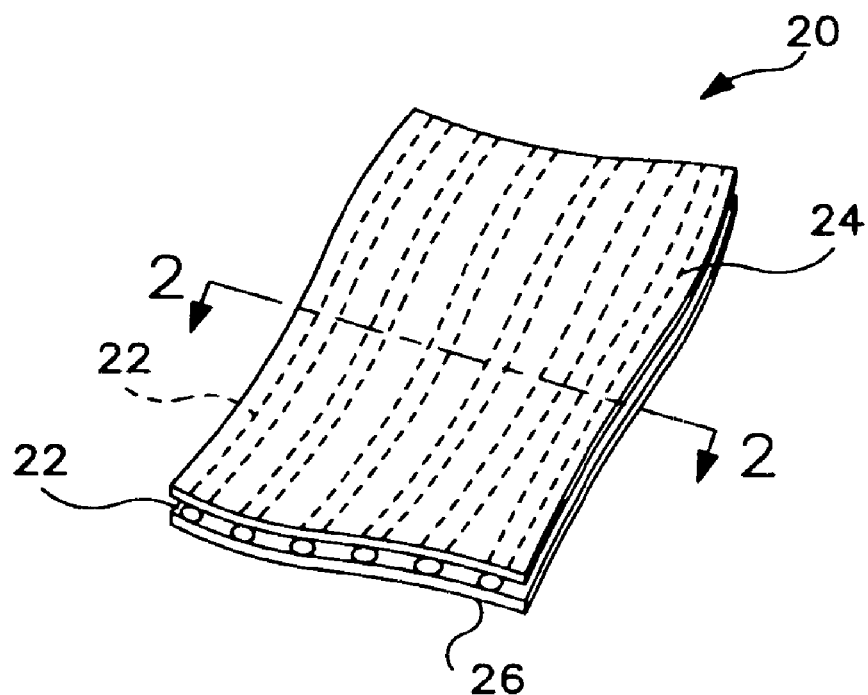
FIG. 1 is a plan view of one embodiment of an elastic strand laminate of the invention.

Within the context of this specification, each term or phrase below will include the following meaning or meanings. "Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastic tension" refers to the amount of force per unit width required to stretch an elastic material (or a selected zone thereof) to a given percent elongation.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Elongation" refers to the capability of an elastic material to be stretched a certain distance, such that greater elongation refers to an elastic material capable of being stretched a greater distance than an elastic material having lower elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Garment" includes personal care garments, medical garments, and the like. The term "disposable garment" includes garments which are typically disposed of after 1–5 uses. The term "personal care garment" includes diapers, training pants, swim wear, absorbent underpants, adult incontinence products, feminine hygiene products, and the like. The term "medical garment" includes medical (i.e., protective and/or surgical) gowns, caps, gloves, drapes, face masks, and the like. The term "industrial workwear garment" includes laboratory coats, cover-alls, and the like.

"High softening point tackifier" refers to a tackifier having a softening point above 80 degrees Celsius, and a viscosity of at least 1500 cps at 360 degrees Fahrenheit as measured by a ring and ball method (ASTM E-28).

"Layer" when used in the singular can have the dual meaning of a single element or a plurality of elements.

"Low softening point additive" refers to a tackifier or wax or low molecular weight polymers having a softening point below 80 degrees Celsius, and a viscosity of less than 1000 cps at 360 degrees Fahrenheit as measured by a ring and ball method (ASTM E-28).

"Melt tank processable" refers to a composition that can be processed in conventional hot melt equipment rather than in an extruder. Hot melt equipment can be used online, such as in a diaper machine, whereas extruders are used offline due to equipment restrictions.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Softening point" refers to a material softening temperature, typically measured by a ring and ball type method, ASTM E-28.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Strand" refers to an article of manufacture whose width is less than a film and is suitable for incorporating into a film, according to the present invention. More particularly, a strand may be thread-like with a cylindrical cross-section, for example, or may be flat or ribbon-like with a rectangular cross-section, for example.

"Stretch-to-stop" refers to a ratio determined from the difference between the unextended dimension of a composite elastic material and the maximum extended dimension of a composite elastic material upon the application of a specified tensioning force and dividing that difference by the unextended dimension of the composite elastic material. If the stretch-to-stop is expressed in percent, this ratio is multiplied by 100. For example, a composite elastic material having an unextended length of 12.7 cm (5 inches) and a maximum extended length of 25.4 cm (10 inches) upon applying a force of 2000 grams has a stretch-to-stop (at 2000 grams) of 100 percent. Stretch-to-stop may also be referred to as "maximum non-destructive elongation".

"Thermoplastic" describes a material that softens and flows when exposed to heat and which substantially returns to a non-softened condition when cooled to room temperature.

"Vertical filament stretch-bonded laminate" or "VF SBL" refers to a stretch-bonded laminate made using a continuous vertical filament process, as described herein.

These terms may be defined with additional language in the remaining portions of the specification.

DETAILED DESCRIPTION OF THE PRESENTLY PREFERRED EMBODIMENTS

The present invention is directed to an elastic strand laminate having superior elastic and adhesion properties, and a method of making such laminates. The laminate can be incorporated into any suitable article, such as personal care garments, medical garments, and industrial workwear garments. More particularly, the elastic strand laminate is suitable for use in diapers, training pants, swim wear, absorbent underpants, adult incontinence products, feminine hygiene products, protective medical gowns, surgical medical gowns, caps, gloves, drapes, face masks, laboratory coats, and coveralls.

A number of elastomeric components are known for use in the design and manufacture of such articles. For example, disposable absorbent articles are known to contain elasticized leg cuffs, elasticized waist portions, and elasticized fastening tabs. The elastic strand laminate of this invention may be applied to any suitable article to form such elasticized areas.

An elastic strand laminate of the invention includes a plurality of strands formed from an elastomeric adhesive composition. The elastomeric adhesive composition includes a base polymer and a high softening point tackifier resin. The composition may also include a low softening point additive and/or an antioxidant. The choice of polymer and tackifier is important, as is the ratio of polymer or copolymers to tackifier. Another important consideration is the ratio of low softening point additive to high softening point tackifier.

The base polymer suitably has a styrene content of between about 15% and about 45%, or between about 18% and about 30%, by weight of the base polymer. The base polymer may achieve the styrene content either by blending different polymers having different styrene co-monomer levels or by including a single base polymer that has the desired styrene co-monomer level. Generally, the higher the styrene co-monomer level is, the higher the tension is.

The base polymer may include polystyrene-polyethylene-polypropylene-polystyrene (SEPS) block copolymer, styrene-isoprene-styrene (SIS), styrene-butadiene-styrene (SBS) block copolymer, thermoplastic polyurethane, ethylene-propylene-diene (EPDM) copolymer, as well as combinations of any of these. One example of a suitable SEPS copolymer is available from Kraton Polymers of Belpre, Ohio, under the trade designation KRATON® G 2760. One example of a suitable SIS copolymer is available from Dexco, a division of Exxon-Mobil, under the trade designation VECTOR™. Suitably, the composition includes the base polymer in an amount between about 30% and about 75% by weight of the composition.

The base polymer suitably has a Shore A hardness of between about 20 and about 90, or between about 30 and about 80. Shore A hardness is a measure of softness, and can be measured according to ASTM D-5.

In one embodiment of the invention, the base polymer may have a melt flow rate between about 5 and about 200 grams per minute, Shore A hardness between about 20 and about 70, and may be stretched up to about 1300%.

The tackifier may include hydrocarbons from petroleum distillates, rosin, rosin esters, polyterpenes derived from wood, polyterpenes derived from synthetic chemicals, as well as combinations of any of these. A key element of the composition from which the strands are made is a high softening point tackifier. An example of a suitable high softening point tackifier is available from Hercules Inc. of Wilmington, Del., under the trade designation PICO-LYTE™ S115. Suitably, the composition includes the high softening point tackifier in an amount between about 30% and about 70% by weight of the composition.

A low softening point additive may be included in the compositions as well. A low softening point additive typically has a softening point below 80 degrees Celsius and a viscosity of less than 1000 cps at 360 degrees Fahrenheit, while a high softening point tackifier typically has a softening point above 80 degrees Celsius and a viscosity of at least 1500 cps at 360 degrees Fahrenheit. The use of predominantly high softening point tackifiers with high viscosity is important for adhesion improvement due to enhanced cohesive strength. However, the inclusion of relatively low amounts of low softening point additives provides instantaneous surface tackiness and pressure sensitive characteristics as well as reduced melt viscosity. Suitably, the low softening point additive is present in the composition in an amount between about 0% and about 20% by weight of the composition. One example of a particularly suitable low softening point additive is PICOLYTE™ S25 tackifier, available from Hercules Inc., having a softening point in a range around 25 degrees Celsius, or paraffin wax having a melting point of about 65 degrees Celsius may also be used.

Additionally, an antioxidant may be included in the composition, suitably in an amount between about 0.1% and about 1.0% by weight of the composition. One example of a suitable antioxidant is available from Ciba Specialty Chemicals under the trade designation IRGANOX™ 1010.

Viscosity of the formulated elastomeric adhesive composition is suitably in the range of 5,000 to 80,000 cps at 350 to 400 degrees Fahrenheit, or 10,000 to 50,000 cps at between 350 and 385 degrees Fahrenheit. The adhesive composition can be processed by conventional hot melt equipment.

Figure 2:
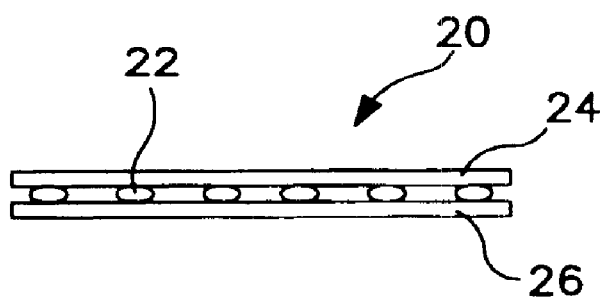
FIG. 2 is a cross-sectional view, taken along line 2—2 of FIG. 1, of an elastic strand laminate of the invention.

One embodiment of an elastic strand laminate 20 of the invention is shown in FIG. 1. The strands 22 may be self-adhered to at least one facing sheet, or between a first facing sheet 24 and a second facing sheet 26 as shown. A cross-sectional view of the laminate 20 in FIG. 1 is shown in FIG. 2. It will be appreciated that the strands 22 may be laid out periodically, non-periodically, and in various spacings, groupings, and sizes, according to the effect desired from the elastic strand laminate 20 and the use to which it is put. For example, the strands 22 may be spaced apart to between about 5 and about 15 strands per inch.

The strands 22 are substantially continuous in length. The strands 22 may have a circular cross-section, but may alternatively have other cross-sectional geometries such as elliptical, rectangular as in ribbon-like strands, triangular or multi-lobal. Each strand 22 suitably has a diameter between about 0.1 and about 0.25 inch, with "diameter" being the widest cross-sectional dimension of the strand.

The strands 22 made of the elastomeric adhesive composition are capable not only of introducing a degree of elasticity to facing materials 24, 26 but are also capable of providing a construction adhesive function. That is, the strands adhere together the facing materials or other components with which they are in contact. It is also possible that the strands do not constrict upon cooling but, instead, tend to retract to approximately their original dimension after being elongated during use in a product.

Facing materials 24, 26 may be nonwoven webs or polymer films formed using conventional processes, including the spunbond and meltblowing processes described in the DEFINITIONS. For example, the facing sheets 24, 26 may each include a spunbonded web having a basis weight of about 0.1–4.0 ounces per square yard (osy), suitably 0.2–2.0 osy, or about 0.4–0.6 osy. The facing sheets 24, 26 may include the same or similar materials or different materials.

If the facing sheets 24, 26 are to be applied to the strands 22 without first being stretched, the facing sheets may or may not be capable of being stretched in at least one direction in order to produce an elasticized area. For example, the facing sheets could be necked, or gathered, in order to allow them to be stretched after application of the strands. Various post treatments, such as treatment with grooved rolls, which alter the mechanical properties of the material, are also suitable for use. The laminate 20 suitably has a basis weight between about 20 and about 120 grams per square meter.

Figure 3:
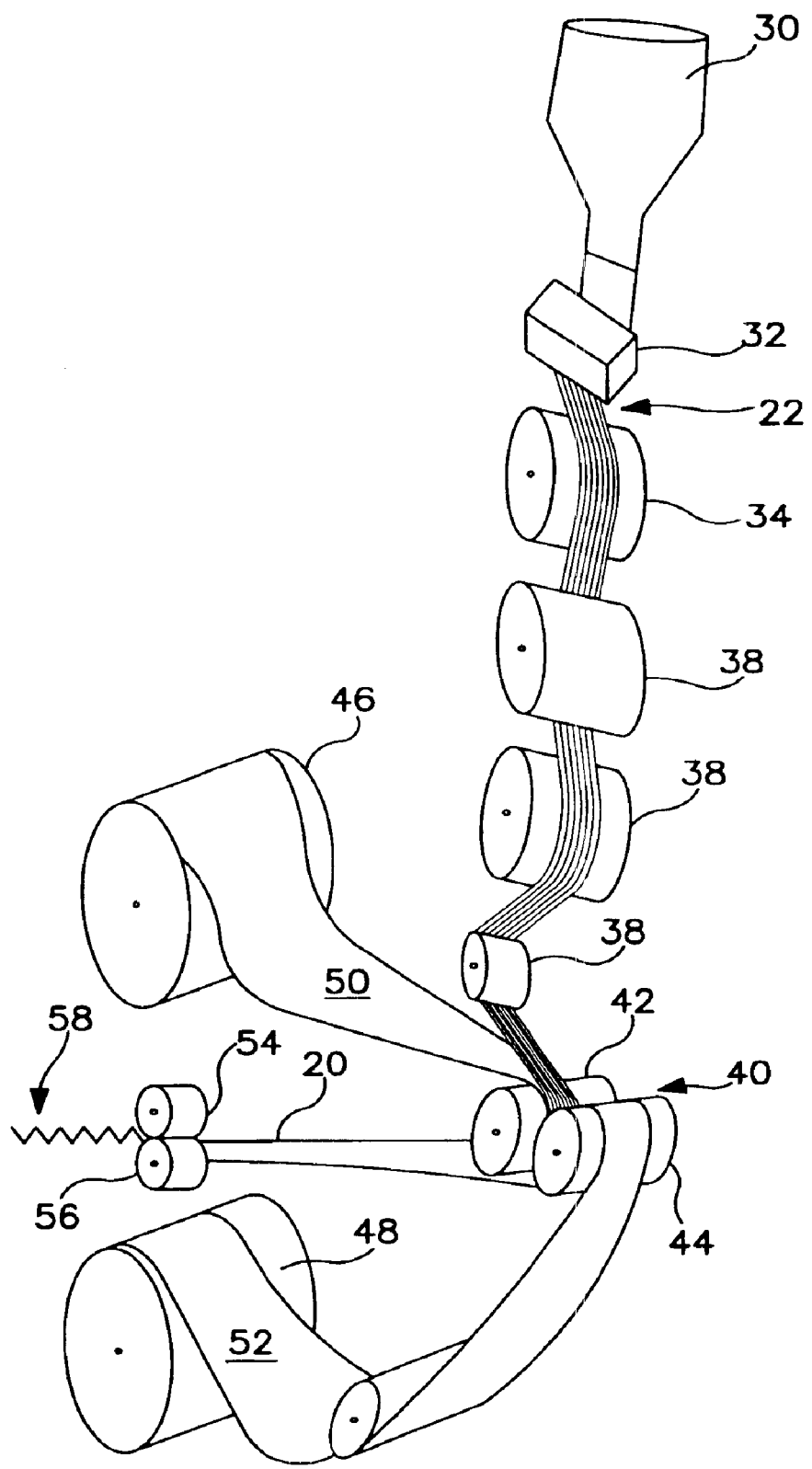
FIG. 3 illustrates a representative process for making the elastic strand laminates of the invention.

FIG. 3 illustrates a method and apparatus for making an elastic strand laminate 20 of the invention. While FIG. 3 illustrates a composite VF SBL process it will be appreciated that other processes consistent with the present invention may be used.

The elastomeric adhesive composition is formulated by mixing the base polymer and the tackifier in a Sigma blade batch mixer or by other suitable compounding methods including continuous mixing processes such as twin screw extrusion, resulting in a solid phase composition. Conventional hot melt equipment can be used to heat the composition. For example, solid blocks of the composition may be heated in a melt tank 30 at about 385 degrees Fahrenheit, for example, to form a liquid phase, and then processed through a strand die 32 at between about 20 and about 150 grams per square meter (gsm), or between about 40 and about 100 gsm output before stretching, onto a first chill roll 34 or similar device at between about 10 and about 55 degrees Celsius, for example, in the form of multiple strands 22. Strand output (gsm) denotes grams per square meter as measured by cutting the strands with a template and weighing them. The strands 22 are then stretched (between about 200% and about 1200%) and thinned as the strands are peeled off the first chill roll 34 and passed to one or more fly rollers 38 towards a nip 40. The strands 22 may be stretched down to a narrower width and thinned by the fly rollers 38 during their passage to the nip 40. The nip 40 is formed by opposing first and second nip rollers 42, 44.

The configuration of the strand die 32 determines the number of strands, diameter of the strands, spacing between the strands, as well as shape of the strands.

The elastomeric adhesive composition in the form of strands 22 suitably has an elongation of at least 50 percent, alternatively of at least 150 percent, alternatively of from about 50 percent to about 500 percent, and a tension force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width. Tension force, as used herein, is determined one minute after stretching the elastic strand laminate to 100% elongation.

In order to form the elastic strand laminate 20, first and second rolls 46 and 48, respectively, of spunbond facing material 50, 52 or other nonwoven or film are fed into the nip 40 on either side of the strands 22 and are bonded by the adhesive present in the strands 22. The facing material 50, 52 might also be made in situ rather than unrolled from previously made rolls of material. While illustrated as having two lightweight gatherable spunbond facings 50, 52, it will be appreciated that only one facing material, or various types of facing materials, may be used. The elastic strand laminate 20 can be maintained in a stretched condition by a pair of tensioning rollers 54, 56 downstream of the nip 40 and then relaxed as at Ref. No. 58 (FIG. 3).

Figure 4:
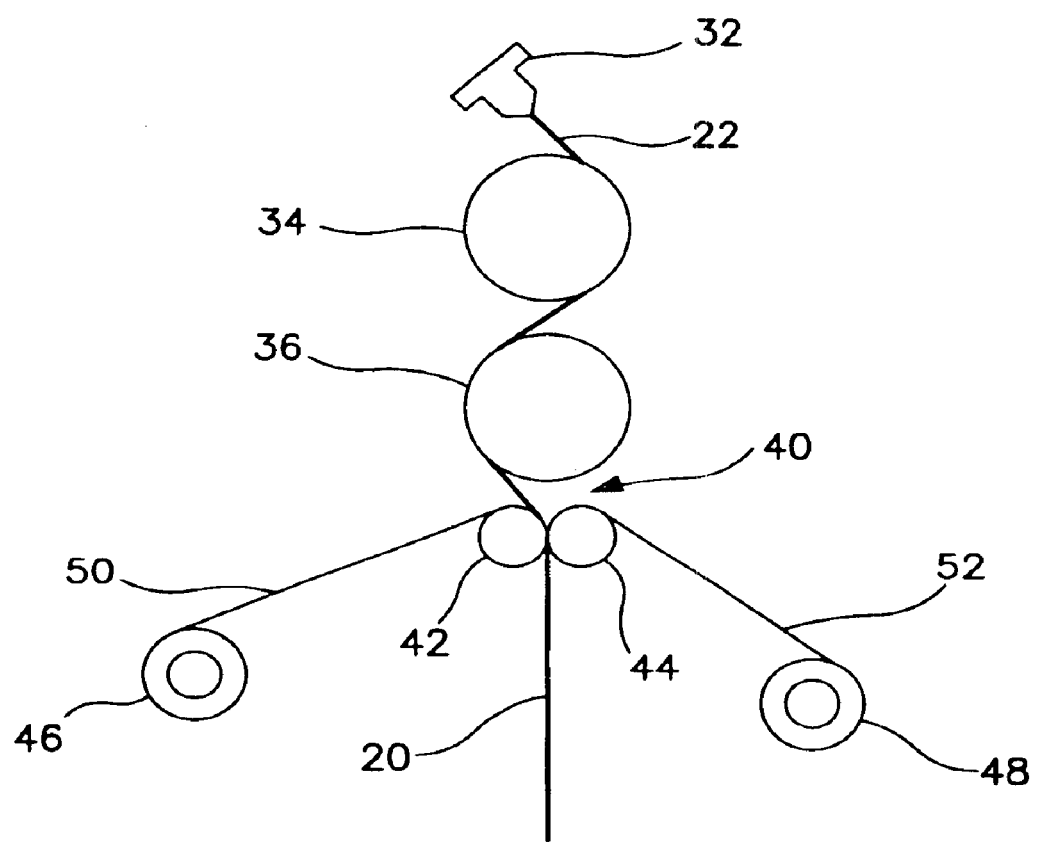
FIG. 4 is a schematic view of another process for making the elastic strand laminates of the invention.

FIG. 4 illustrates a VF SBL process in which no fly rollers 38 are used. Instead, the elastomeric adhesive composition in the form of strands 22 is extruded onto chill roller 34. The strands are stretched between chill rollers 34 and 36 and the nip 40. Except for the lack of fly rollers, the processes of FIGS. 3 and 4 are similar. In either case, the strands 22 can be laminated between a first facing layer 50 and a second facing layer 52 at the nip 40.

Tension within the laminate 20 may be controlled through varying the percentage stretch, or stretch ratio, of the strands 22 prior to adhesion to the facing sheet(s), and/or through the amount of strand add-on or thickness, with greater stretch and greater add-on or thickness each resulting in higher tension. Tension can also be controlled through selection of the elastomeric adhesive composition, and/or by varying strand geometries and/or spacing between strands. For example, holes in the strand die 32 through which the composition passes to form strands may vary in diameter. The laminate of the invention suitably has tension of at least 100 grams/inch at 100% elongation, or at least 200 grams/inch at 100% elongation.

Figure 5:
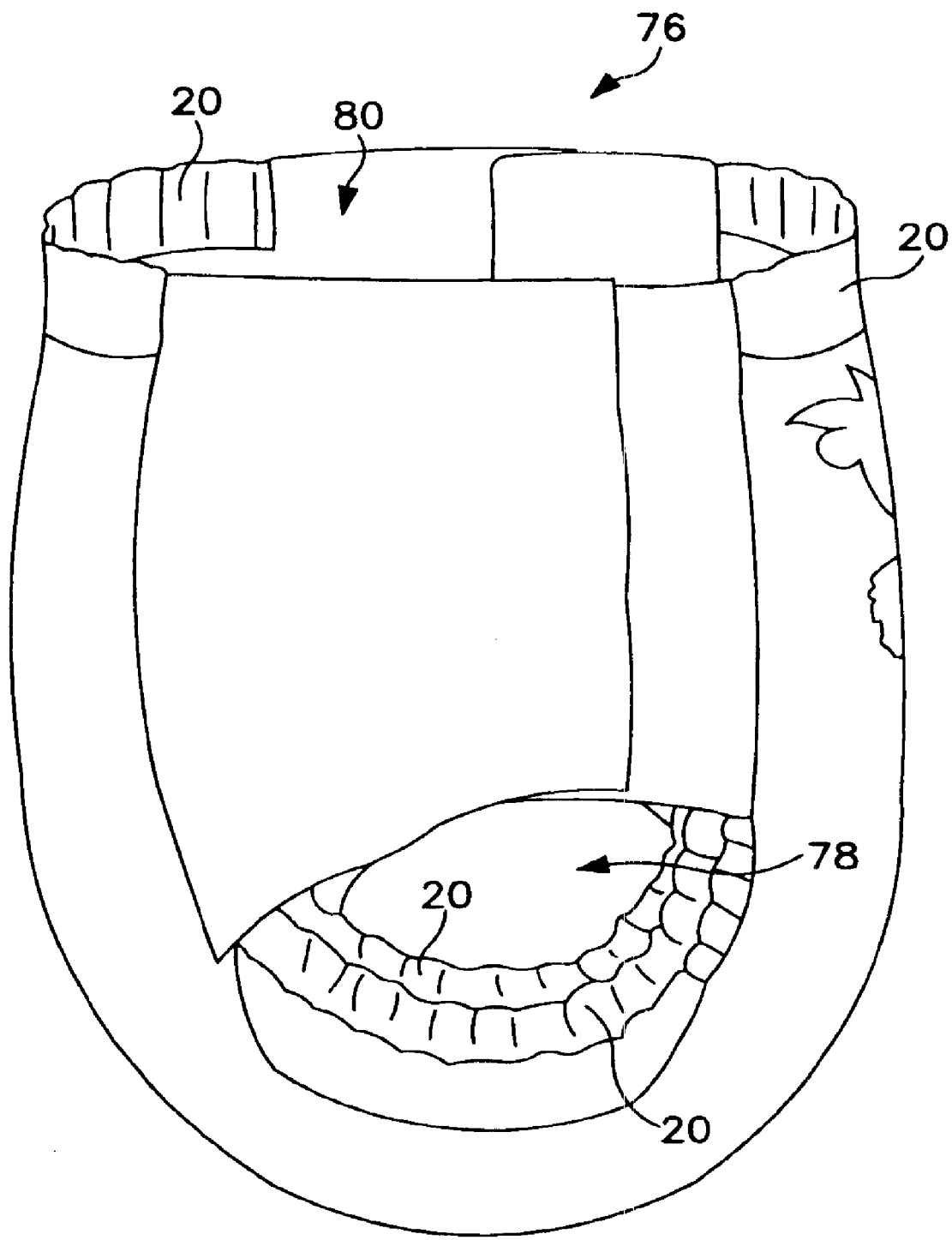
FIG. 5 is a perspective view of a garment having an elastic strand laminate around the leg openings and waist opening.

The resulting elastic strand laminate 20 is particularly useful in providing elasticity in personal care absorbent garments 76, as shown in FIG. 5. More specifically, as shown in FIG. 5, the elastic strand laminate 20 is particularly suitable for use in providing a gasket-like fit around leg openings 78 and waist openings 80. The laminates of this invention are less likely to undergo tension decay or delamination compared to similar laminates incorporating current commercial elastomeric adhesive compositions, as demonstrated in the examples below. Also demonstrated in the examples below is the laminate's relatively high stretch-to-stop ratio, suitably at least 50%, or at least 100%, or at least 150%, or at least 250%, and the relatively low creep, suitably less than 10% creep after aging at 100 degrees Fahrenheit for 90 minutes.

TEST METHODS

Elongation

The elongation of an elastic composite laminate according to the present invention is suitably determined as follows. A 1-inch wide by 4-inch long sample of the laminate is provided. The central 3-inch (7.62 cm) area of the sample is marked. The test sample is then stretched to its maximum length, and the distance between the marks is measured and recorded as the "stretched to stop length." The percent elongation is determined according to the following formula:

$$\{(\text{stretched to stop length (in inches)})-3\}/3\times 100$$

If a 1-inch by 4-inch area is not available, the largest sample possible (but less than 1-inch by 4-inches) is used for testing with the method being adjusted accordingly.

Tension Force

The tension force of an elastic composite laminate according to the present invention is determined on a test sample of the laminate having a width of 1 inch (2.54 cm) and a length of 3 inches (7.62 cm). A test apparatus having a fixed clamp and an adjustable clamp is provided. The adjustable clamp is equipped with a strain gauge commercially available from S. A. Mieier Co. under the trade designation Chatillon DFIS2 digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 100 percent of its elongation (as determined by the test method set forth above). The tension force is read from the digital force gauge after 1 minute. At least three samples of the elasticized area are tested in this manner with the results being averaged and reported as grams force per inch width.

Creeping Resistance of Elastic Strands

Figure 6:
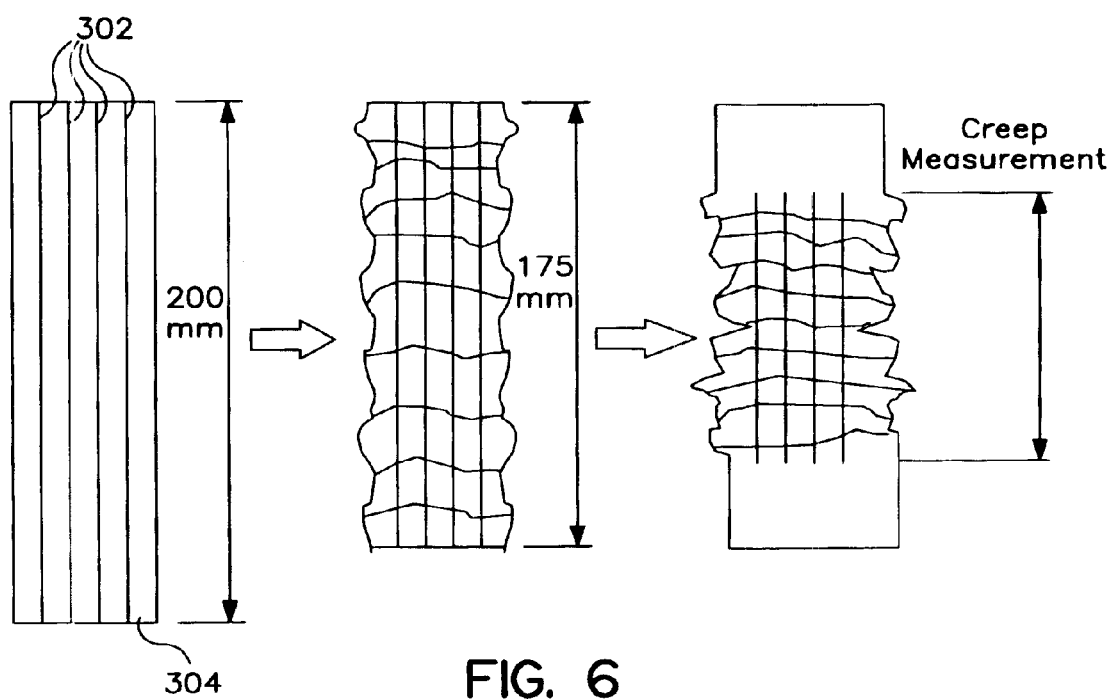
FIG. 6 shows a schematic diagram of creep testing.

Twelve elastic strands 302, approximately 2.5 mm apart in the cross-direction and each elongated approximately 300%, were adhesively attached and sandwiched between two 4-inch wide continuous polypropylene spunbonded layers 304 to form a laminate. The laminate was fully extended by hanging a weight (about 500 grams or higher) at one end of the laminate, and a 200 mm machine-direction length was then marked. The laminate was then released, such that the 200 mm length snapped back to 175 mm, whereupon the 175 mm length was marked. The laminate was then stapled to a piece of cardboard at the 175 mm length. The marked length of the laminate was then cut to release tension in the elastic strands 302, and the snapback length of the strands was measured. An illustration of the creeping test procedure is shown in FIG. 6.

Initial creep percentage was calculated by first determining the difference between the 175 mm length and the snapback length, then dividing the difference by the 175 mm length and multiplying the quotient by 100, as shown in the following equation:

$$\text{Initial Creep \%}=(175_{mm}-X_{initial\ creep})/175\times 100$$

The sample was then placed in an oven at 100 degrees Fahrenheit for 90 minutes to measure aging creep. Aging creep percentage was then calculated by determining the difference between the 175 mm length and that snapback length, then dividing the difference by the 175 mm length and multiplying the quotient by 100, as shown in the following equation:

$$\text{Aging Creep \%}=(175_{mm}-Y_{aged\ creep})/175\times 100$$

$X_{initial\ creep}$ and $Y_{aged\ creep}$ readings were taken from the averaged measurements of the 24 strands during the tests.

EXAMPLE 1

In this example, several formulations of the elastomeric adhesive composition used in the invention were tested for tension decay and/or adhesion.

Composition 1

In this example, the formulated elastomeric adhesive composition was made up of 55 wt % VECTOR™ 4111 SIS polymer and 45 wt % ESCOREZ™ 5340 tackifier, both available from Exxon-Mobil. ESCOREZ™ 5340 has a softening point of 140 degrees Celsius and viscosity of 5000 cps at 177 degrees Celsius. The composition had an output of 89 gsm before stretching, and was stretched to 600%.

Adhesion of the elastomeric adhesive composition was tested by laminating the composition between two 0.6 osy spunbond facings. A 2-inch wide sample of the laminate, tested at 50% elongation, had a green tension of 136 grams and a permanent set of 12.3%. It was found that no delamination occurred after 2 weeks of aging at 130 degrees Fahrenheit, under a laminate tension of 81.7 grams. After 2 weeks under these conditions, tension loss of the laminate was 40%, and permanent set was 15.7%.

Composition 2

Another elastomeric adhesive composition was made up of 48 wt % VECTOR™ 4111 SIS polymer, 9 wt % VECTOR™ 4411 SIS polymer, 38 wt % ESCOREZ™ 5340 tackifier, and 5 wt % paraffin wax. This composition had 120 gsm film output before stretching, and was stretched to 800%. The composition was laminated between two 0.6 osy spunbond facings after being extruded through a film die.

An Instron tester, or Sintech tester, or similar instrument, was used to measure tension of a 2-inch sample of the laminate at room temperature. The tension in the laminate during a first cycle was determined to be 167.9 grams (g) at 5.0% elongation. During retraction of the first cycle, the tension in the laminate was determined to be 68.1 g. The laminate experienced a hysteresis loss of 59.4%. A permanent set for cycle 1 was 18.7%, and a permanent set for cycle 2 was 21%. High permanent set indicates poor elasticity, while low permanent set indicates good elasticity. The laminate experienced no delamination after 2 weeks at 130 degrees Fahrenheit.

Composition 3

This composition had the same formulation as the previous composition, but included ESCOREZ™ 5415 tackifier in place of ESCOREZ™ 5340 tackifier. ESCOREZ™ 5415 has a lower softening point of 118 degrees Fahrenheit, and a lower viscosity of 900 cps at 177 degrees Celsius. Consequently, when tested in the same manner as the previous compositions, namely between two 0.6 osy spunbond facings, this composition was found to have poor adhesion qualities, with the laminate delaminating in 24 hours.

Composition 4

This composition had the same formulation as the two previous compositions, but included ESCOREZ™ 5320 tackifier in place of either ESCOREZ™ 5340 tackifier or ESCOREZ™ 5415 tackifier. ESCOREZ™ 5320 has a relatively low softening point of 122 degrees Celsius, and a relatively low viscosity of 1500 cps at 177 degrees Celsius. Consequently, when tested in the same manner as the previous compositions, namely between two 0.6 osy spunbond facings, this composition was found to have poor adhesion qualities, with the laminate delaminating in 24 hours.

Composition 5

In this example, the formulated elastomeric adhesive composition was made up of 65 wt % KRATON® G 2760 SEPS copolymer, available from Kraton Polymers, and 35 wt % PICOLYTE™ S115 tackifier, available from Hercules Inc. The materials were formulated in a Sigma blade batch mixer. The Brookfield viscosity of the formulation was determined to be about 51,000 cps at 380 degrees Fahrenheit. Solid blocks of the adhesive were heated in a melt tank at 385 degrees Fahrenheit and slot coated on a chill roll at 52 degrees Celsius. The process involved peeling off the film from the chill roll while stretching the material up to about 700% at 47 gsm output (before stretching) from the slot coat die. The stretched film was then laminated by nip roll with two nonwoven spunbond webs on each side in a continuous manner.

The laminate appeared to be soft and elastomeric. The green tension value, as measured quickly off-line was in the range of 170–190 grams/inch width. Specifically, 5-inch long specimens were clamped and elongated to 100%. The tension reading was recorded from an electronic gauge one minute after clamping. The tension remaining in the laminate was 100–110 grams/inch width after aging at 130 degrees Fahrenheit for 22 hours. No delamination was observed even after aging at 130 degrees Fahrenheit for an excess of 4 days.

EXAMPLE 2

A series of formulated compositions were produced to compare the effects of low softening point tackifiers versus high softening point tackifiers. A variety of tackifiers having various softening points were used in various combinations, summarized in Table 1. The tackifiers used were:

PICOLYTE™ S25, available from Hercules Inc., having a softening point of 15–25 degrees Celsius, and viscosity of 1,000 cps at 80 degrees Celsius;

PICOLYTE™ S115, available from Hercules Inc., having a softening point of 115 degrees Celsius, and viscosity of 10,000 cps at 150 degrees Celsius; and STAYBELITE™ 5, available from Hercules Inc., having a softening point of 79 degrees Celsius.

These formulated compositions were laminated with 0.6 osy spunbond facings and were then tested for tension decay and delamination. The tension decay was measured by first measuring the "green" tension at 100% elongation of a 2-inch wide, 5-inch long sample. The tension reading was recorded from an electronic gauge one minute after clamping. After aging the samples at 130 degrees Fahrenheit for 1 day, the "aged" tension was then measured in the same manner as the green tension and the resulting aged tension was compared to the green tension to determine whether, or to what extent, tension decay occurred.

It was found that low softening point tackifier alone in the formulation not only caused poor bonding because of low cohesion but also generated low green tension and high tension decay. Results are shown in Table 1.

TABLE 1

Comparison of Tackifiers in Elastic Composite Laminates

| | Tackifier Composition (percentage of total tackifier included in composition) | | | |
|---|---|---|---|---|
| Sample | PICO-LYTE™ S25 | PICO-LYTE™ S115 | STAY-BELITE™ 5 | Observations |
| 1 | 100% | — | — | Delaminated in 10 minutes |
| 2 | — | 100% | — | No delamination |
| 3 | 25% | 75% | — | Green tension decreased 20–40%; tension decay was more than 60% after aging at 130° F. for 22 hours; delaminated within 24 hours |
| 4 | 25% | — | 75% | Green tension = 210 g/in width; 100% tension decay after aging at 130° F. for 22 hours; delaminated within 24 hours |

These results confirm that high softening point tackifiers are critical for elastomeric adhesive tension control and adhesion improvement in addition to base polymer choice.

EXAMPLE 3

In this example, a self-adhering elastic strand laminate of the invention was formed by creating an elastomeric adhesive composition including 50 wt % VECTOR™ 4111 SIS polymer, 10 wt % VECTOR™ 4411 SIS polymer, 39.5 wt % ESCOREZ™ 5340 tackifier, each available from Exxon-Mobil, and 0.5% IRGANOX™ 1010 antioxidant, available from Ciba Specialty Chemicals. The elastomeric adhesive composition was formulated in a Sigma blade mixer or compounded by a twin screw extruder. The Brookfield viscosity of the formulation was about 66,500 cps at 385 degrees Fahrenheit. A solid block form of the adhesive was heated in a melt tank at 385 degrees Fahrenheit and extruded from a strand die onto a chill roll at 52 degrees Fahrenheit, stretching the strands up to about 500% at 28 gsm output.

The strand die was 12 inches wide, with 12 strands per inch each having a diameter of 50 mil. The laminate was then formed by nipping the strands between two 0.5 osy nonwoven spunbond webs.

Initial tension in the laminate was 103 grams per square inch ($g/in^2$) at 50% elongation. The laminate tension remained at 85 $g/in^2$ after aging at 130 degrees Fahrenheit for a week. No delamination was observed even after aging at 130 degrees Fahrenheit for a week.

EXAMPLE 4

In this example, it was shown that a strand-laminate provides more tension than a film laminate. Furthermore, the strand laminates in this example showed better tension retention after aging than the film laminates. Consequently, the strand laminates provide required tension for product application at a much lower add-on level as indicated by the much higher ratio of tension (g) to film or strand output (gsm) as shown in Table 2.

Each of the laminates tested were tested using a 2-inch wide sample with two facings of 0.5 osy PRISM bi-component material, available from Kimberly-Clark Corporation. A description of PRISM is taught in U.S. Pat. No. 5,336,552 to Strack et al., herein incorporated by reference. Two different film laminates and two different strand laminates were formed from the elastomeric adhesive composition described in the previous example, with the samples varying in terms of output and/or stretch.

The strand laminates exhibited much lower tension decay in terms of low tension loss percentage after aging compared to the film laminates. The lower tension loss and lower tension relaxation of the strand laminates, compared to the film laminates, indicates that the strand laminates had better elastic properties. Detailed results of strand laminates and film laminates are shown in Table 2.

TABLE 3

Comparison of SIS Polymer-Based Strand Laminates to Other Laminates

| Sample | Note | Stretch-to-Stop % | Creep % after aging at 100 degrees F. 90 min |
|---|---|---|---|
| Strand 1 | 55% VECTOR ™ 4111, 45% ESCOREZ ™ 5340, 800% stretch, 53 gsm output, 0.5 osy spunbond facings | 230% | ~0% |
| Strand 2 | 50% VECTOR ™ 4111, 10% VECTOR ™ 4411, 39.5% ESCOREZ ™ 5340, and 0.5% IRGANOX ™ 1010, 500% stretch, 28 gsm, 0.5 osy PRISM facings | 270% | <10% |
| VFL-SBL | KRATON ™ 6631 using extruder, H2096 adhesive add-on 4–10 gsm, 0.5 osy spunbond facings | ~170% | ~30% |
| LYCRA ™ | LYCRA ™ 940, strand from DuPont, H2525A adhesive, add-on 7–10 gsm, 0.5 osy spunbond facings | 150–180% | 20–50% dependent on applications |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this

TABLE 2

Comparison of Strand and Film Laminates

| Sample Identification | Ratio of Tension (g/output) gsm) | Initial Tension ($g/in^2$ at 50% elongation) | Tension after aging at 130 degrees F., one week | Tension loss % after aging | Tension relaxation % at 50%, 30 min |
|---|---|---|---|---|---|
| Film laminate (90 gsm before stretch; 700% stretch) | 1.33 | 120 | 71 | 41 | 42 |
| Strand laminate (28 gsm before stretch, 700% stretch) | 2.61 | 73 | 63 | 14 | 36 |
| Film laminate (120 gsm before stretch, 700% stretch) | 1.14 | 137 | 81 | 41 | 40 |
| Strand laminate (28 gsm before stretch, 500% stretch) | 3.68 | 103 | 85 | 17.5 | 38 |

EXAMPLE 5

In this example, two elastic strand laminates of the invention were compared to a VFL-SBL laminate and a LYCRA laminate in terms of creep percentage and stretch-to-stop properties. Creep percentage was measured according to the test method described above. The higher stretch-to-stop ratio and lower creep percentage of the strand laminates indicates better elasticity and adhesion properties. Results are shown in Table 3.

invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An elastic laminate, comprising:

at least one facing sheet; and a plurality of strands of a melt-tank processable elastomeric construction adhesive composition self-adhered to the at least one facing sheet;

the elastomeric adhesive composition including at least 55% by weight of a base polymer selected from the group consisting of polystyrene-polyethylene-polypropylene-polystyrene (SEPS) block copolymer, styrene-isoprene-styrene (SIS) block copolymer, styrene-butadiene-styrene (SBS) block copolymer, thermoplastic polyurethane, ethylene-propylene-diene copolymers, and combinations thereof, and at least 30% by weight of a high softening point tackifier resin comprising at least one type of hydrocarbon selected from the group consisting of petroleum distillates, rosin, rosin esters, polyterpenes derived from wood, polyterpenes derived from synthetic chemicals, and combinations thereof, and having a softening point of at least 80 degrees Celsius and a viscosity of at least 1500 cps at 182 degrees Celsius;

wherein the elastomeric construction adhesive composition has a viscosity of about 5,000 to 80,000 cps at between 177 and 204 degrees Celsius.

2. The elastic strand laminate of claim 1, wherein the plurality of strands are spaced apart on the at least one facing sheet by about 2 to about 6 strands per centimeter.

3. The elastic strand laminate of claim 1, wherein each of the plurality of strands has a diameter between 0.25 and 0.64 centimeter.

4. The elastic strand laminate of claim 1, wherein the at least one facing sheet comprises a nonwoven web selected from a spunbond web and a meltblown web.

5. The elastic strand laminate of claim 1, wherein the at least one facing sheet comprises a film.

6. The elastic strand laminate of claim 1, wherein the base polymer has a melt flow rate between about 5 and about 200 grams per minute, a Shore A hardness between about 20 and about 70, and may be stretched up to about 1300%.

7. The elastic strand laminate of claim 1, wherein the elastomeric adhesive composition further comprises a low softening point additive having a softening point of less than 80 degrees Celsius and a viscosity of less than 1000 cps at 182 degrees Celsius, present in an amount between about 0% and about 20% by weight.

8. The elastic strand laminate of claim 1, wherein the elastomeric adhesive composition further comprises an antioxidant in an amount between about 0.1% and about 1.0% by weight.

9. The elastic strand laminate of claim 1, wherein the composition has a viscosity of about 10,000 to 50,000 cps at between 177 and 196 degrees Celsius.

10. The elastic strand laminate of claim 1, wherein e laminate has a basis weight between about 20 and about 120 grams per square meter.

11. The elastic strand laminate of claim 1, wherein the laminate exhibits a stretch-to-stop ratio of at least 50%.

12. The elastic strand laminate of claim 1, wherein the laminate exhibits a stretch-to-stop ratio of at least 150%.

13. The elastic strand laminate of claim 1, wherein the laminate exhibits a stretch-to-stop ratio of at least 250%.

14. The elastic strand laminate of claim 1, wherein the laminate has tension of at least 100 grams per inch at 100% elongation.

15. The elastic strand laminate of claim 1, wherein the laminate has tension of at least 200 grams per inch at 100% elongation.

16. An elastic laminate, comprising:

a first facing sheet and a second facing sheet; and a plurality of strands of an elastomeric construction adhesive composition self-adhered between the first facing sheet and the second facing sheet, and spaced apart by about 2 to about 6 strands per centimeter;

the elastomeric adhesive composition including at least 55% by weight of a base polymer selected from the group consisting of polystyrene-polyethylene-polypropylene-polystyrene (SEPS) block copolymer, styrene-isoprene-styrene (SIS), styrene-butadiene-styrene (SBS) block copolymer, thermoplastic polyurethane, ethylene-propylene-diene (EPDM) copolymer, and combinations thereof; and at least 30% by weight of a high softening point tackifier resin comprising at least one type of hydrocarbon selected from the group consisting of petroleum distillates, rosin, rosin esters, polyterpenes derived from wood, polyterpenes derived from synthetic chemicals, and combinations thereof, and having a softening point of at least 80 degrees Celsius and a viscosity of at least 1500 cps at 182 degrees Celsius;

wherein the elastomeric construction adhesive composition has a viscosity of about 5,000 to 80,000 cps at between 177 and 204 degrees Celsius and the spaced apart strands have diameters of at least 0.25 centimeter.

17. The elastic strand laminate of claim 16, wherein at least one of the first and second facing sheets comprises a nonwoven web selected from a spunbond web and a meltblown web.

18. The elastic strand laminate of claim 16, wherein at least one of the first and second facing sheets comprises a film.

19. The elastic strand laminate of claim 16, wherein the elastomeric adhesive composition further comprises a low softening point additive having a softening point of less than 80 degrees Celsius and a viscosity of less than 1000 cps at 182 degrees Celsius.

20. The elastic strand laminate of claim 16, wherein the elastomeric adhesive composition further comprises an antioxidant in an amount between about 0.1% and about 1.0% by weight.

21. The elastic strand laminate of claim 16, wherein the laminate exhibits less than 10% creep after aging at 38 degrees Celsius for 90 minutes.

22. The elastic strand laminate of claim 16, wherein the laminate exhibits a stretch-to-stop ratio of at least 200%.

* * * * *

UNITED STATES PATENT AND TRADEMARK OFFICE
CERTIFICATE OF CORRECTION

PATENT NO.   : 6,967,178 B2
DATED         : November 22, 2005
INVENTOR(S)  : Peiguang Zhou et al.

It is certified that error appears in the above-identified patent and that said Letters Patent is hereby corrected as shown below:

<u>Column 15,</u>
Line 55, delete "e" and insert -- the --.

Signed and Sealed this

Seventh Day of February, 2006

JON W. DUDAS
*Director of the United States Patent and Trademark Office*